United States Patent
Keller

(10) Patent No.: US 9,480,543 B2
(45) Date of Patent: Nov. 1, 2016

(54) DISPENSING DEVICE WITH A SPRAY ASSEMBLY

(75) Inventor: Wilhelm A. Keller, Merlischachen (CH)

(73) Assignee: Medmix Systems AG, Rotkreuz (CH)

( * ) Notice: Subject to any disclaimer, the term of this patent is extended or adjusted under 35 U.S.C. 154(b) by 1076 days.

(21) Appl. No.: 12/227,017

(22) PCT Filed: Apr. 23, 2007

(86) PCT No.: PCT/CH2007/000193
§ 371 (c)(1),
(2), (4) Date: Nov. 5, 2008

(87) PCT Pub. No.: WO2007/131371
PCT Pub. Date: Nov. 22, 2007

(65) Prior Publication Data
US 2009/0230214 A1    Sep. 17, 2009

(30) Foreign Application Priority Data
May 17, 2006    (CH) .......................................... 803/06

(51) Int. Cl.
| | | |
|---|---|---|
| B05B 1/34 | (2006.01) | |
| B67D 7/70 | (2010.01) | |
| A61C 9/00 | (2006.01) | |
| A61C 5/06 | (2006.01) | |
| B05B 7/04 | (2006.01) | |

(52) U.S. Cl.
CPC ............. A61C 9/0026 (2013.01); A61C 5/064 (2013.01); B05B 1/3436 (2013.01); B05B 7/0408 (2013.01); B05B 7/0416 (2013.01)

(58) Field of Classification Search
CPC .. A61C 5/064; A61C 9/0026; B05B 7/0416; B05B 7/0408; B05B 1/3436
USPC ................... 239/463; 222/137, 145.1, 145.6; 604/191, 366, 83, 84, 86, 144, 147
See application file for complete search history.

(56) References Cited

U.S. PATENT DOCUMENTS

| | | | | |
|---|---|---|---|---|
| 3,191,872 A | * | 6/1965 | Dyson | ............................ 241/74 |
| 3,441,081 A | * | 4/1969 | Carr et al. | ...................... 165/74 |
| 4,117,551 A | * | 9/1978 | Brooks et al. | ............ 366/162.1 |
| 4,251,032 A | | 2/1981 | Werding | |
| 4,260,110 A | | 4/1981 | Werding | |
| 4,538,920 A | * | 9/1985 | Drake | ........................ 366/181.5 |

(Continued)

FOREIGN PATENT DOCUMENTS

| | | |
|---|---|---|
| EP | 0 096 731 A1 | 12/1983 |
| GB | 2 351 459 A | 1/2001 |

(Continued)

OTHER PUBLICATIONS

Translation of Official Action issued in Japanese patent application No. 2009-510251; mailed May 29, 2012; 2 pages.

*Primary Examiner* — Arthur O Hall
*Assistant Examiner* — Steven M Cernoch
(74) *Attorney, Agent, or Firm* — Foley & Lardner LLP

(57) ABSTRACT

The spray assembly of a dispensing device is arranged together with a mixing assembly inside a mixing and spray head, the mixing assembly being arranged before the swirl chamber of the spray assembly, and the mixing and spray head, which forms a unit, being removably attached to a multicomponent dispensing appliance. The result is a more homogeneous spray action, on one hand, and an easy replacement of the head, on the other hand.

24 Claims, 4 Drawing Sheets

(56) References Cited

U.S. PATENT DOCUMENTS

| | | | |
|---|---|---|---|
| 5,064,098 A * | 11/1991 | Hutter et al. | 222/137 |
| 5,067,655 A * | 11/1991 | Farago et al. | 239/124 |
| 5,116,315 A * | 5/1992 | Capozzi et al. | 604/82 |
| 5,190,440 A * | 3/1993 | Maier et al. | 415/174.5 |
| 5,605,255 A | 2/1997 | Reidel et al. | |
| 6,048,201 A * | 4/2000 | Zwingenberger | 433/90 |
| 6,820,766 B2 | 11/2004 | Keller et al. | |
| 7,537,174 B2 * | 5/2009 | Redl et al. | 239/321 |
| 7,635,343 B2 * | 12/2009 | McIntosh et al. | 604/82 |
| 7,748,567 B2 * | 7/2010 | Horner et al. | 222/135 |
| 2004/0074927 A1 * | 4/2004 | Lafond | 222/327 |
| 2007/0012724 A1 * | 1/2007 | Feinberg et al. | 222/137 |
| 2007/0164047 A1 * | 7/2007 | Reidt et al. | 222/137 |
| 2007/0175921 A1 * | 8/2007 | Keller | 222/137 |
| 2007/0228076 A1 * | 10/2007 | Horner et al. | 222/135 |

FOREIGN PATENT DOCUMENTS

| | | |
|---|---|---|
| JP | 54059613 A | 5/1979 |
| JP | 7163925 A | 6/1995 |
| JP | 9187637 A | 7/1997 |
| JP | 2923448 B2 | 4/1999 |

* cited by examiner

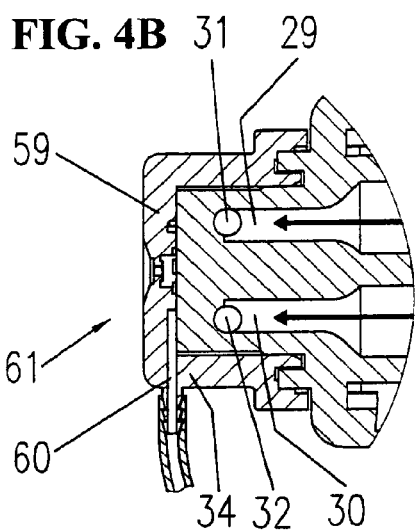
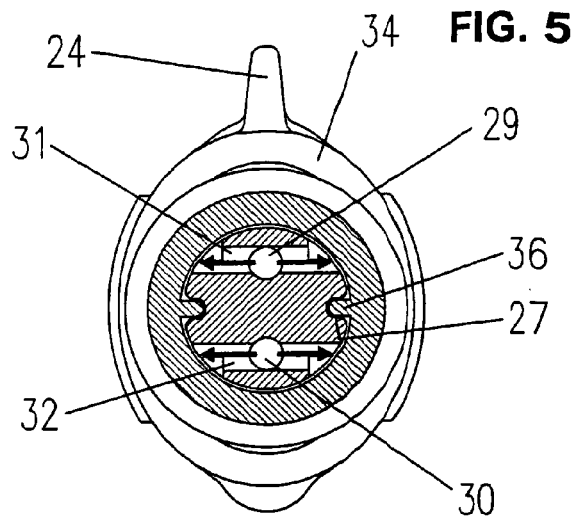
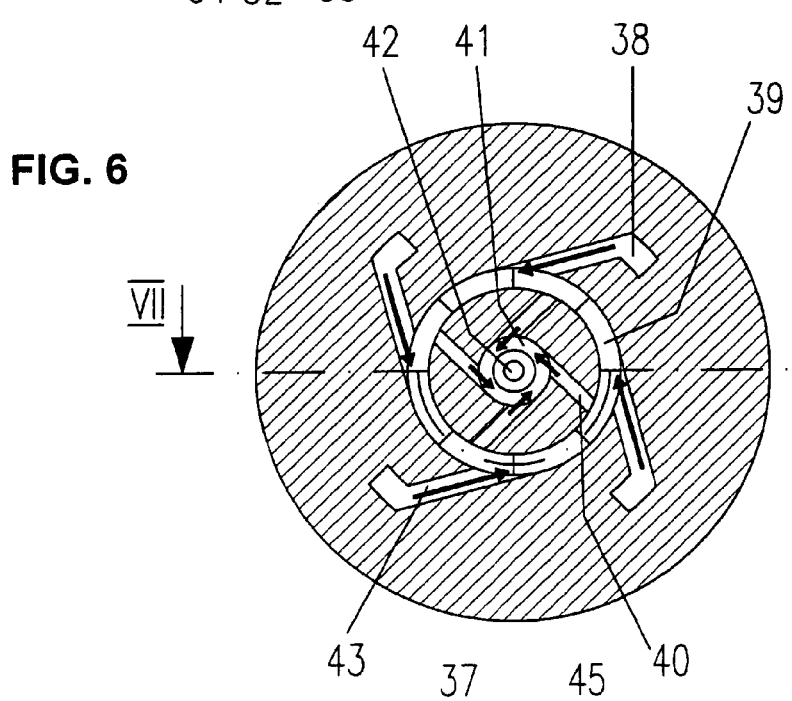
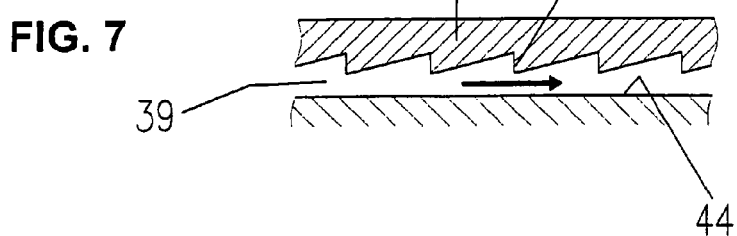

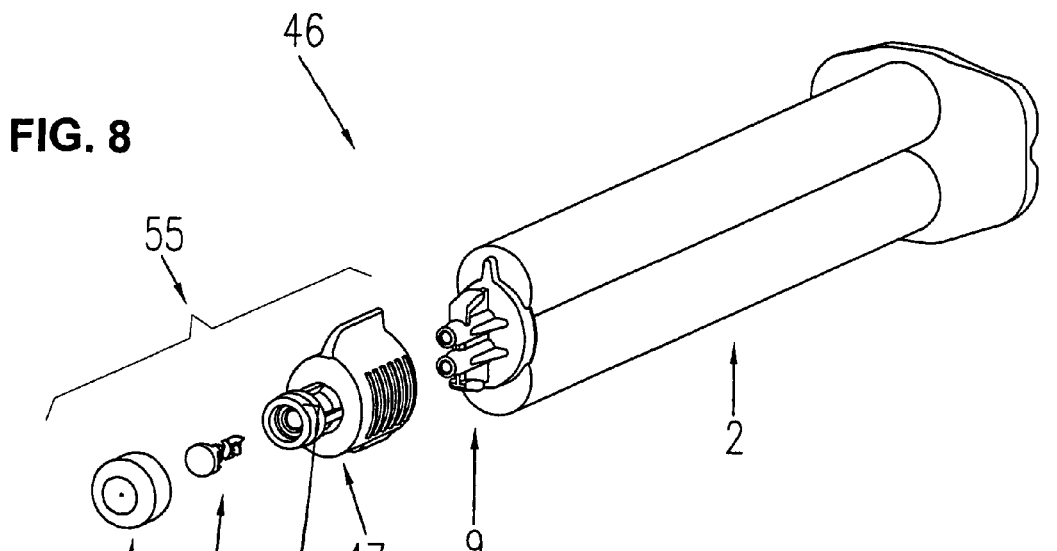
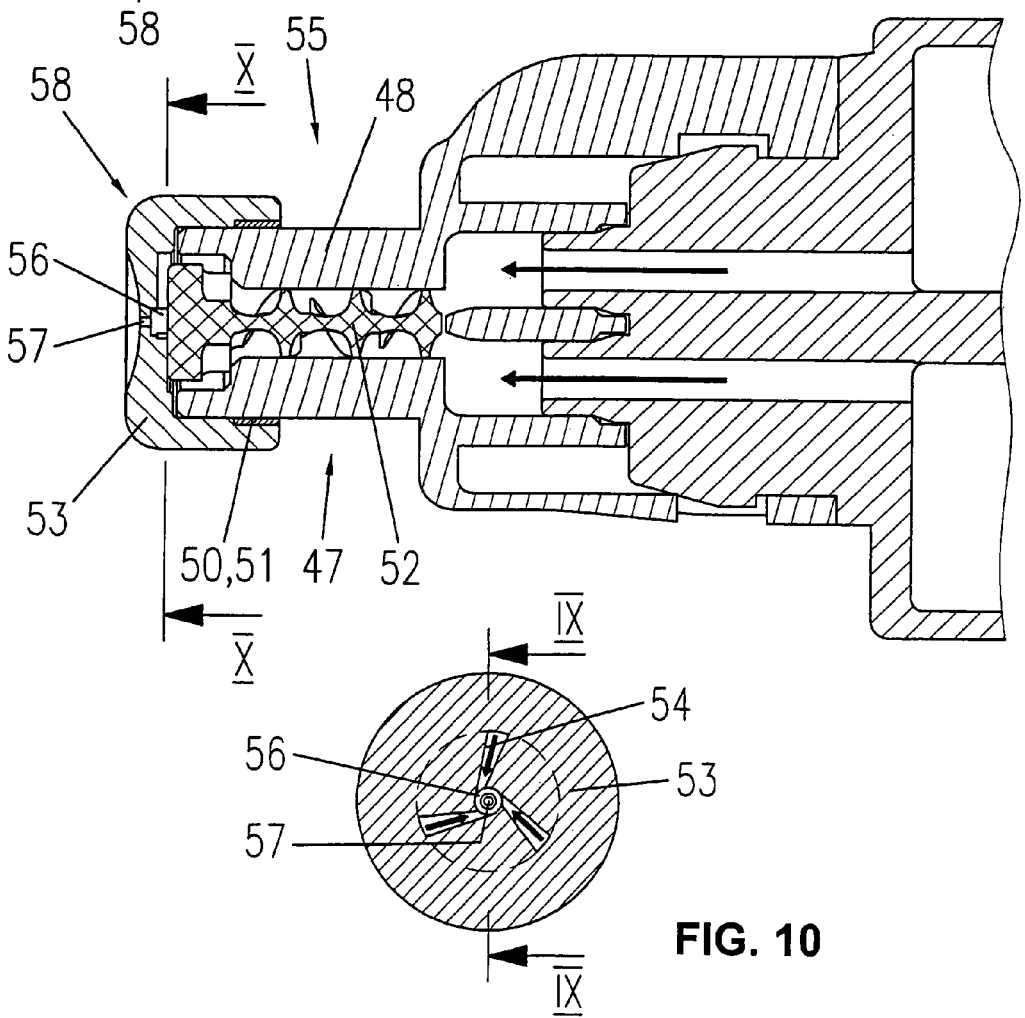

DISPENSING DEVICE WITH A SPRAY ASSEMBLY

This application is the National Phase of PCT/CH2007/000193, filed Apr. 23, 2007, which claims priority to Switzerland Application No. 00803/06, filed May 17, 2006, the disclosures of which are hereby incorporated by reference in their entirety.

The present invention relates to a dispensing device with a spray assembly according to the preamble of claim 1. A device of this kind is e.g. known from U.S. Pat. No. 4,260,110, which patent mainly relates to the design of a spray nozzle, however. This patent specification only discloses dispensing devices having a spray nozzle for a single component.

BACKGROUND OF THE INVENTION

For certain medical applications, however, two-component materials are stored in double syringes or double cartridges, mixed by means of static mixers and dispensed using different application instruments. For large surface dispensing or when a distribution of the mixed materials by means of an applicator is not possible, a spraying system has to be used. In conventional spray assemblies, the two-component materials are only mixed to a limited extent or compressed air is additionally required which in certain operations leads to undesirable aerosol formation and does not always ensure a homogeneous distribution of the two components on the sprayed surface.

SUMMARY OF THE INVENTION

On this background, it is the object of the present invention to provide a dispensing device by means of which two or more components are homogenously mixed prior to their entry into the spray nozzle. In addition, as the components harden after having been mixed and sprayed, the mixing and spray assembly should be exchangeable in the simplest possible manner. This is accomplished by the dispensing device according to claim 1.

The invention will be explained in more detail hereinafter with reference to drawings of exemplary embodiments.

BRIEF DESCRIPTION OF THE DRAWINGS

FIG. 4B shows a partial view of an embodiment variant of the mixing and spray piece of FIG. 4A with a compressed air inlet, FIG. 5 shows a section according to line V-V in FIG. 4, FIG. 6 shows a section according to line VI-VI in FIG. 4, FIG. 7 shows a section according to line VII-VII in FIG. 6, FIG. 8 shows a second exemplary embodiment of a dispensing device according to the invention in a perspective view, FIG. 9 shows a section through the assembled mixing and spray head of FIG. 8, and FIG. 10 shows a section according to line X-X in FIG. 9.

DETAILED DESCRIPTION

Figure 1A:
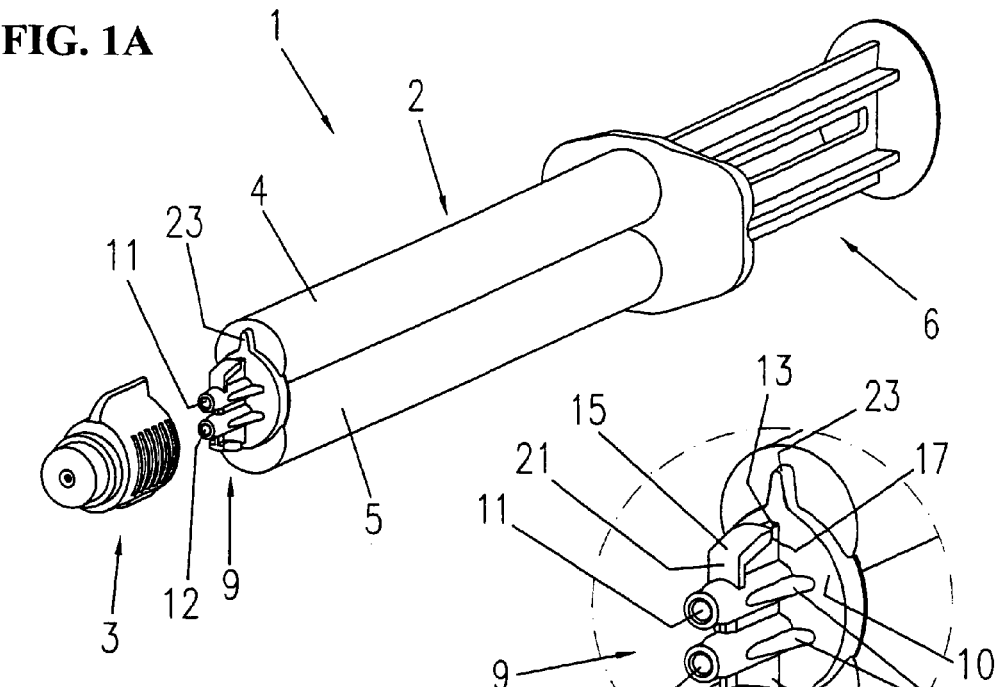
FIGS. 1A and 1B show a first exemplary embodiment of a dispensing device according to the invention in a perspective view.
Figure 1B:
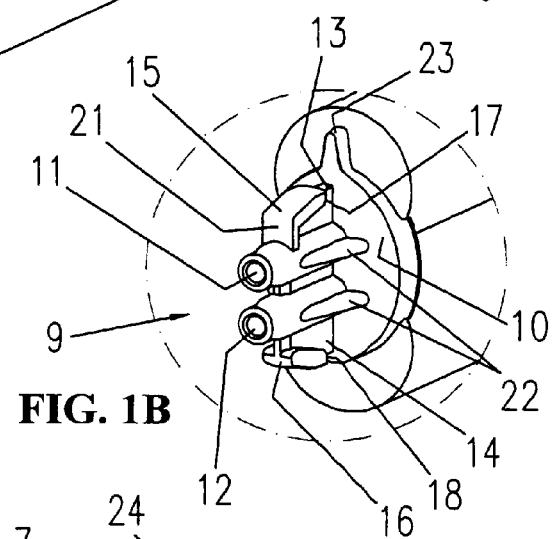

Dispensing device 1 according to FIGS. 1A and 1B includes a double syringe 2 and a mixing and spray head 3 that is attachable thereto. In a known manner, the double syringe comprises two storage containers 4 and 5 having equal volumes or equal cross-sectional areas, respectively, or cross-sectional areas whose ratio is different from 1:1. The two components are dispensed by means of a double plunger 6.

Mixing and spray head 3, hereinafter called "head" for the sake of simplicity, is essentially composed of three parts, namely a transfer housing 7 and a mixing and spray piece 8 that may be connected to the transfer housing by snap means, welding, cementing, a screw connection or by means of a bayonet coupling.

Basically, the head may be coupled to the dispensing appliance in different ways, for example by bayonet coupling means or by a screw connection. Advantageously, however, the head is simply plugged onto the dispensing appliance and easily removable therefrom by a connection as it is described in Swiss patent application no. 00453/06 to the applicant of the present invention. To this end, fastening area 9 on the outlet side of the dispensing appliance has an outlet flange 10 on which the two individual outlets 11 and 12 are arranged. Each outlet 11 and 12 has an essentially diametrically arranged, outwardly directed ridge 13 respectively 14 that tapers from outlet flange 10 toward the outlet. Each ridge has a saddle portion 15 respectively 16 that ends at a distance from the outlet flange and is followed there by a snap nose 17 respectively 18, the snap noses engaging in recesses 19 and 20 in transfer housing 7, see FIG. 4A.

The two saddle portions 15 and 16 have the same configuration, but saddle portion 15 has an end portion 21 on the outlet side while saddle portion 16 has none. The presence or absence of end portion 21 constitutes a coding means ensuring that the head can only be attached in an unequivocal orientation. Furthermore, on both sides of their connecting plane, the two outlets are provided with clamping guides 22. Additionally, outlet flange 10 has a visual coding nose 23 that serves as an orientation aid for the head, the latter having a corresponding orientation nose 24.

Figure 2:
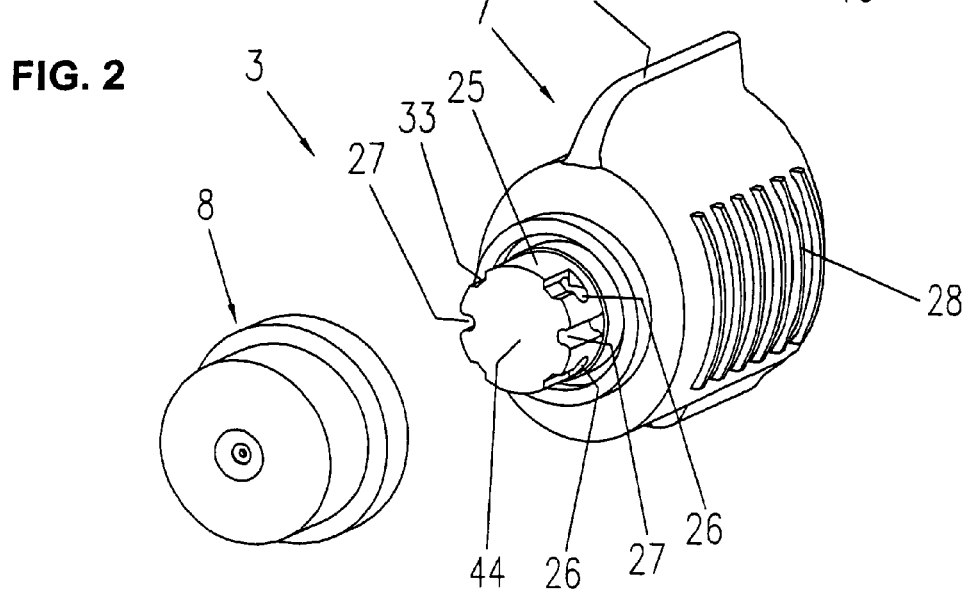
FIG. 2 shows an enlarged detail of FIG. 1.
Figure 3:
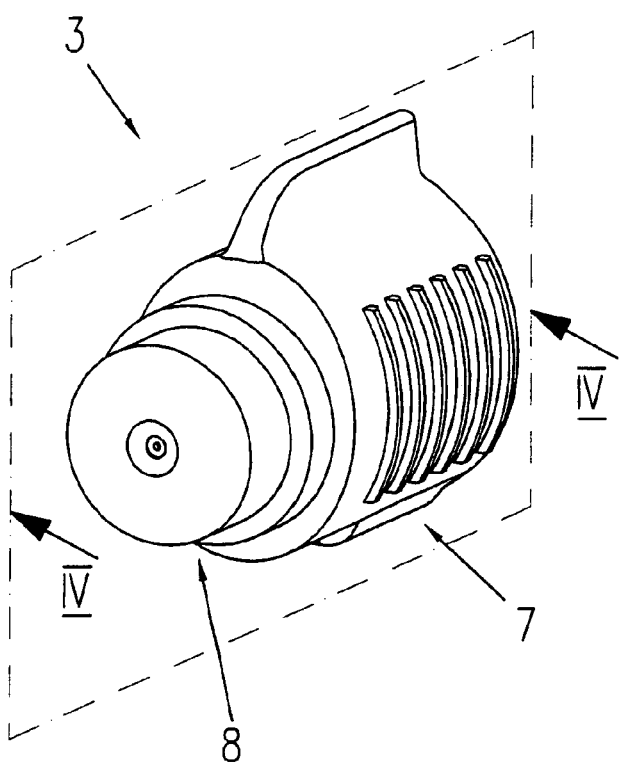
FIG. 3 shows the mixing and spray head of FIG. 2 in the assembled condition.

In FIG. 2, a head 3 consisting of two component parts is illustrated where mixing and spray piece 8 is fastened to transfer housing 7 while the end of the latter forms rear chamber bottom wall 44 of the mixing and swirl chambers. At its outlet side end, transfer housing 7 has a distributor socket 25 in which four distributor outlets 26 and two positioning grooves 27 are arranged. In the area of corrugation 28, the housing is compressible in order to disengage snap noses 17 and 18 from recesses 19 and 20, thereby allowing to withdraw the head.

Figure 4A:
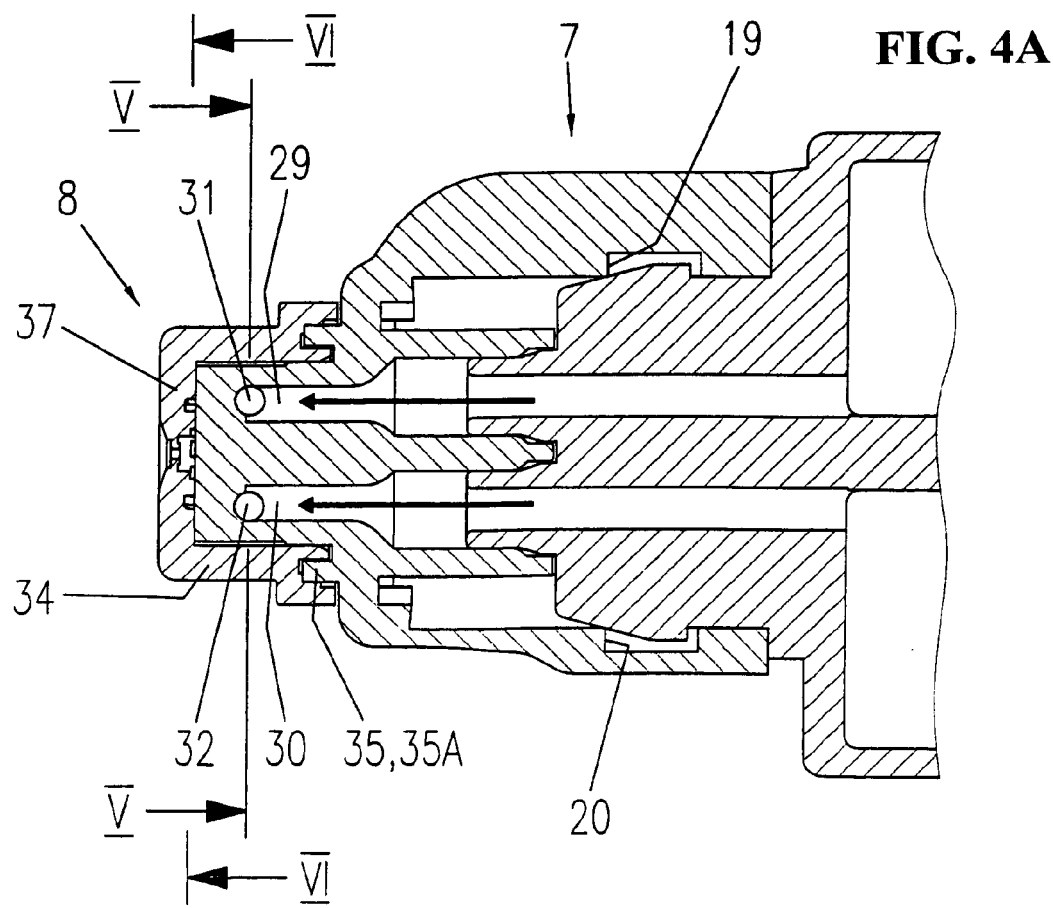
FIG. 4A shows a section according to line IV-IV in FIG. 3.

As follows from FIG. 4A, two longitudinal bores 29 and 30 are arranged in the distributor socket which communicate with transversal bores 31 and 32, these transversal bores leading to distributor outlets 26. The coding and orientation noses allow plugging the head onto the dispensing appliance in such a manner that longitudinal bores 29 and 30 are in line with outlets 11 and 12 of the dispensing appliance.

As appears in FIG. 2, longitudinal feed passages 33 extend from ends 26 of the transversal bores. In FIG. 4A it is shown that coupling portion 34 of mixing and spray piece 8 has a circumferential groove 35 for receiving a corresponding collar 35A on the transfer housing. Housing portion 34 further comprises two positioning cams 36 which engage in corresponding positioning grooves 27. Closure 37 of mixing and spray piece 8 has four longitudinal channels 38 opening into an annular mixing chamber 39 from where four feed passages 40 lead to a concentric swirl chamber 41 from which spray outlet 42 leads to the exterior. As shown in FIG. 6, the longitudinal feed passages 40 open out tangentially into the swirl chamber 41.

In FIG. 4B, an embodiment variant is illustrated in which a compressed air inlet 60 is arranged on end plate 50 of mixing and spray piece 61 in order to achieve a better spray action in certain cases. The other parts of the head are the same.

In FIG. 6 it is visible that feed passages 40 and feed ducts 43 do not form the same angle with respect to the mixing chamber and are offset from one another. Moreover, the feed passages and the feed ducts and the swirl and mixing chambers, respectively, do not have to be arranged in the same plane with respect to the longitudinal axis of the head.

In FIG. 7 it is apparent that bottom wall 44 of the mixing chamber is plane while at the top, i.e. in closure 37, serrated mixing elements 45 are arranged which produce turbulences in order to mix the two components before they reach the swirl chamber from where they are sprayed through the spray outlet.

As mentioned in the introduction, the present invention essentially aims to provide a mixing assembly before the spray assembly, more particularly before the swirl chamber, in order to achieve an efficient mixture of the components prior to the actual spraying procedure. Instead of providing an annular, concentric mixing chamber having serrated mixing elements, it is also possible according to FIGS. 8 to 10 to provide a mixing assembly comprising a static mixing element as it is known per se.

Dispensing device 46 according to FIG. 8 includes the same dispensing appliance 2 and the same fastening area as in the previous example. The fastening area of transfer housing 47 is the same as in the previous exemplary embodiment whereas mixer socket 48 is configured for receiving a mixing assembly 49 in its interior and fastening means 50, 51 on its exterior in order to attach mixing and spray piece 58 to transfer housing 47, thereby forming mixing and spray head 55.

Mixing assembly 49 with mixing element 52 is fastened in the interior of closure 53 of mixing and spray piece 58 and forms a unit with the latter. Fastening means 50, 51 for the attachment of the mixing and spray piece to transfer housing 47 may be snap, bayonet, or screw connections, or it may be fastened by ultrasonic welding or cementing.

As follows from FIG. 10, closure 53 of the head has feed passages 54 arranged therein, e.g. three of them, which lead to a swirl chamber 56 in the same manner as in the previous example from where spray outlet 57 leads to the exterior. The long feed passages 54 open out tangentially into the swirl chamber 56.

Based on the two exemplary embodiments of a mixing chamber or of a mixing assembly, respectively, other possibilities of mixing assemblies can be designed by one skilled in the art by which the components, whose number may also be greater than two, are efficiently mixed shortly before the swirl chamber prior to being sprayed through the swirl chamber and the spray outlet.

The invention claimed is:

1. A dispensing device comprising a mixing and spray head forming a single unit which is removably attachable to a multicomponent dispensing appliance, the mixing and spray head comprising:

a transfer housing including an end forming a planar bottom wall; and a mixing and spray piece connected to the transfer housing, wherein the mixing and spray piece is separate from the transfer housing;

wherein the mixing and spray piece includes a closure portion covering the planar bottom wall, the closure portion defining a spray outlet, the planar bottom wall facing the spray outlet, wherein an annular mixing chamber is formed in the closure portion opposite the planar bottom wall, the annular mixing chamber being commonly delimited by the closure portion and the planar bottom wall, the annular mixing chamber including serrated mixing elements, the serrated mixing elements being formed in a surface of the closure portion that faces the planar bottom wall, wherein a swirl chamber is formed in the closure portion opposite the planar bottom wall, the swirl chamber being commonly delimited by the closure portion and the planar bottom wall, the swirl chamber being surrounded by the annular mixing chamber, wherein feed ducts are formed in the closure portion opposite the planar bottom wall, the feed ducts being commonly delimited by the closure portion and the planar bottom wall, the feed ducts leading to the annular mixing chamber, wherein a plurality of connecting passages are formed in the closure portion opposite the planar bottom wall, the connecting passages being commonly delimited by the closure portion and the planar bottom wall, the connecting passages leading from the annular mixing chamber to the swirl chamber, and wherein the swirl chamber, the annular mixing chamber, the connecting passages and the feed ducts are arranged in a coplanar manner in a common plane, the common plane extending parallel to the planar bottom wall and perpendicular to a longitudinal axis of the mixing and spray head.

2. The dispensing device according to claim 1, wherein the swirl chamber is arranged concentrically to the annular mixing chamber and opens into the spray outlet.

3. The dispensing device according to claim 1, wherein fastening areas of the multicomponent dispensing appliance and of the transfer housing are configured for an attachment or removal of the mixing and spray head without a relative rotational movement.

4. The dispensing device according to claim 3, wherein the fastening area of the transfer housing is deformable.

5. The dispensing device according to claim 3, wherein the fastening area of the multicomponent dispensing appliance includes snap noses that are engaged in recesses formed in the transfer housing.

6. The dispensing device according to claim 1, wherein the closure portion of the mixing and spray piece includes a compressed air inlet.

7. The dispensing device according to claim 1, wherein the connecting passages open out tangentially into the swirl chamber.

8. The dispensing device according to claim 1, further comprising a multicomponent dispensing appliance to which the mixing and spray head is removably attached.

9. The dispensing device according to claim 1, wherein the connecting passages are offset from the feed ducts.

10. The dispensing device according to claim 1, wherein the annular mixing chamber comprises an annular groove in the closure portion.

11. The dispensing device according to claim 1, wherein the annular mixing chamber, the swirl chamber, the connecting passages and the feed ducts comprise depressions and grooves in the closure portion.

12. The dispensing device according to claim 1, wherein the transfer housing includes a distributor socket, wherein the planar bottom wall is on the distributor socket and wherein the mixing and spray piece connects to the distributor socket.

13. The dispensing device according to claim 12, wherein the mixing and spray piece includes a circumferential coupling portion extending from the closure portion and surrounding the distributor socket.

14. The dispensing device according to claim 13, wherein the distributor socket includes at least two longitudinal bores configured to receive fluid from outlets of the dispensing appliance and at least two transversal bores, wherein each of the at least two longitudinal bores communicates with one of the transversal bores, wherein the at least two transversal bores lead to distributor outlets that open out on an outer circumferential surface of the distributor socket.

15. The dispensing device according to claim 14, wherein the distributor socket includes longitudinal feed passages leading from the distributor outlets to the feed ducts, the longitudinal feed passages being formed in the outer circumferential surface of the distributor socket.

16. The dispensing device according to claim 15, wherein the longitudinal feed passages are delimited commonly by the distributor socket and by the circumferential coupling portion.

17. The dispensing device according to claim 15, wherein the longitudinal feed passages comprise grooves in the outer circumferential surface of the distributor socket.

18. The dispensing device according to claim 1, wherein the serrated mixing elements have a first surface with a first inclination and a second surface with a second inclination,
wherein the first surface is adjacent to the second surface,
wherein the first surface extends from the closure portion towards the planar bottom wall into the annular mixing chamber,
wherein the second surface extends from the annular mixing chamber towards the closure portion, and
wherein the first inclination is bigger than the second inclination.

19. A dispensing device comprising a mixing and spray head forming a single unit which is removably attachable to a multicomponent dispensing appliance, the mixing and spray head comprising:
a transfer housing including a mixer socket defining an interior;
a separate mixing assembly configured to be received in the interior, wherein the mixing assembly includes a mixing element and a disc having a planar bottom wall, the planar bottom wall defining a distal surface that faces away from the mixing element, wherein the mixing element is arranged proximally from the disc and extends from the disc into the interior along a proximal direction, the mixing element having a cross section that is smaller than a cross section of the disc; and
a separate mixing and spray piece fastened to the mixer socket, the mixing and spray piece including a closure portion that covers the planar bottom wall, the closure portion defining a spray outlet, the planar bottom wall facing the spray outlet, wherein the closure portion and the planar bottom wall commonly delimit a swirl chamber, and
wherein a plurality of feed passages lead from the mixing element to the swirl chamber, the plurality of feed passages extending along a lateral surface of the disc and thereafter over the surface of the planar bottom wall to the swirl chamber.

20. The dispensing device according to claim 19, wherein the swirl chamber comprises a depression in the closure portion.

21. The dispensing device according to claim 19, wherein the feed passages comprise grooves in the closure portion.

22. The dispensing device according to claim 19, wherein the mixing assembly comprises a helical mixing element.

23. The dispensing device according to claim 19, wherein the mixer socket includes an exterior with fastening elements and wherein the fastening elements attach the mixing and spray piece to the transfer housing.

24. The dispensing device according to claim 19, wherein the mixing assembly fastens to the closure portion to form a unit with the mixing and spray piece.

* * * * *